(12) United States Patent
Bateman et al.

(10) Patent No.: US 7,077,138 B2
(45) Date of Patent: Jul. 18, 2006

(54) PATIENT VENTILATION DEVICES

(75) Inventors: Timothy Bateman, Dymchurch (GB); John Edward Nash, Hythe (GB); Eric Pagan, Hythe (GB)

(73) Assignee: Smiths Group PLC, London (GB)

( * ) Notice: Subject to any disclaimer, the term of this patent is extended or adjusted under 35 U.S.C. 154(b) by 0 days.

(21) Appl. No.: 09/940,419

(22) Filed: Aug. 29, 2001

(65) Prior Publication Data

US 2002/0033175 A1    Mar. 21, 2002

(30) Foreign Application Priority Data

Sep. 21, 2000   (GB) ................................. 0023250.4

(51) Int. Cl.
*A62B 7/10* (2006.01)
*A62B 18/08* (2006.01)

(52) U.S. Cl. ............................ 128/206.14; 128/206.29

(58) Field of Classification Search ........... 128/202.25, 128/202.28, 204.18, 207.14, 207.15, 207.13, 128/206.24, 206.21, 206.25, 206.28, 206.29, 128/202.29, 203.11, 206.12, 206.23, 207.12, 128/206.14, 205.25; 2/9, 206, 244, 248; D24/110.4, 110.5, 859, 863
See application file for complete search history.

(56) References Cited

U.S. PATENT DOCUMENTS

| | | | | | |
|---|---|---|---|---|---|
| 3,049,121 | A | * | 8/1962 | Brumfield et al. ..... | 128/206.14 |
| 3,695,265 | A | * | 10/1972 | Brevik .................... | 128/206.14 |
| 3,982,532 | A | | 9/1976 | Halldin et al. | |
| 4,050,457 | A | * | 9/1977 | Davidson ................ | 128/202.28 |
| 4,579,114 | A | | 4/1986 | Gray et al. | |
| 4,674,492 | A | | 6/1987 | Niemeyer | |
| 4,711,237 | A | * | 12/1987 | Kaiser .......................... | 128/859 |
| 4,858,605 | A | * | 8/1989 | Levy ...................... | 128/203.11 |
| 5,088,485 | A | * | 2/1992 | Schock ................... | 128/202.28 |
| 5,265,595 | A | | 11/1993 | Rudolph | |
| 5,476,092 | A | * | 12/1995 | Karlis et al. ........... | 128/203.11 |
| 5,511,543 | A | * | 4/1996 | Shirley ................... | 128/203.11 |
| 5,666,950 | A | * | 9/1997 | Smith ..................... | 128/207.14 |
| 6,082,360 | A | | 7/2000 | Rudolph et al. | |
| 6,196,223 | B1 | | 3/2001 | Belfer et al. | |
| 2002/0092526 | A1 | * | 7/2002 | Bertoch et al. ......... | 128/207.17 |

FOREIGN PATENT DOCUMENTS

| | | |
|---|---|---|
| DE | 23063 A | 4/1962 |
| DE | 4004157 | 4/1991 |
| FR | 1309878 | 10/1962 |
| WO | 99/25140 | 5/1999 |
| WO | WO 99/25410 | 5/1999 |

* cited by examiner

*Primary Examiner*—Teena Mitchell
(74) *Attorney, Agent, or Firm*—Louis Woo

(57) ABSTRACT

A ventilation device has a flexible adhesive sheet that can be sealed around the patient's nose and mouth. A fitting extending through the sheet in the region of the mouth enables the patient to be ventilated by means of a vent tube inserted through the fitting.

7 Claims, 2 Drawing Sheets

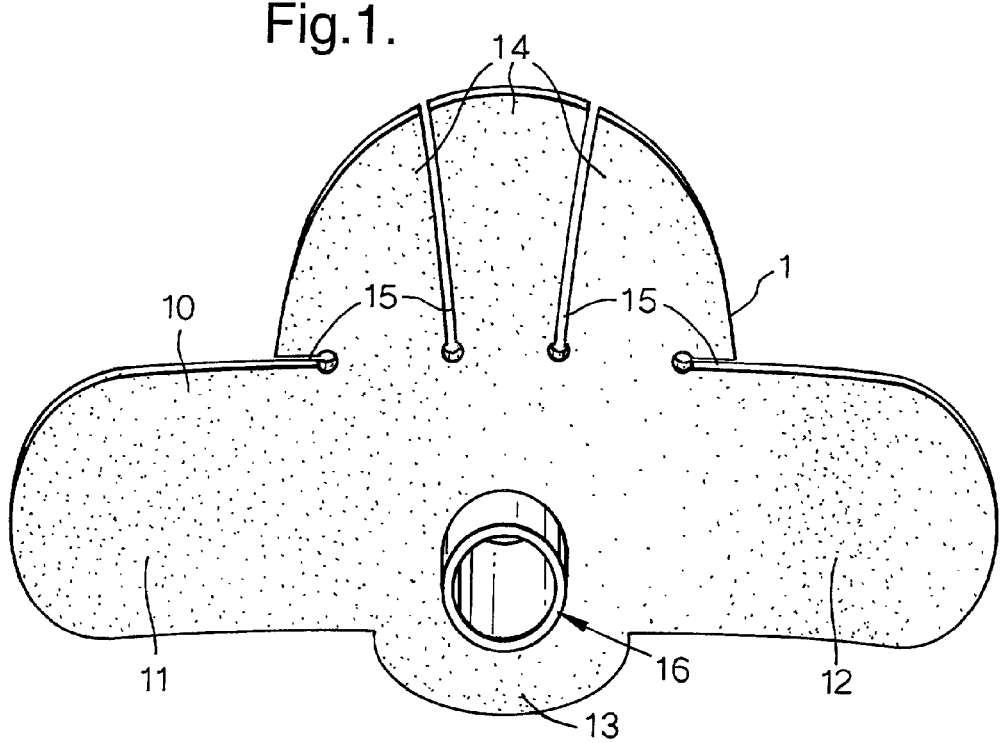
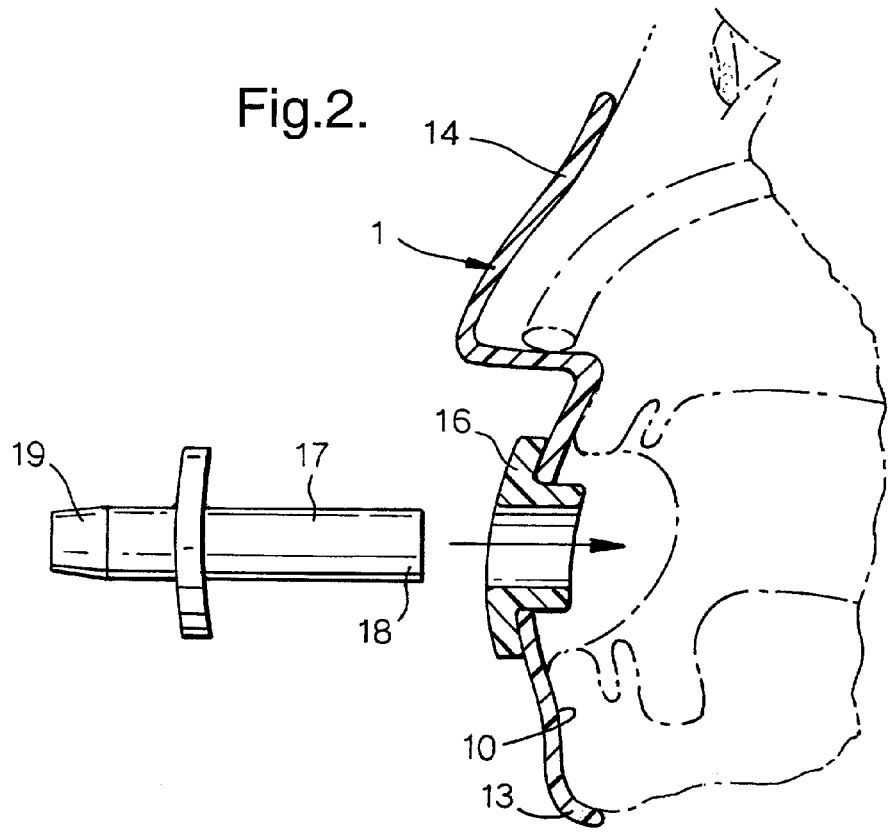

PATIENT VENTILATION DEVICES

BACKGROUND OF THE INVENTION

This invention relates to patient ventilation devices.

The invention is more particularly concerned with face masks for use in ventilating patients.

Conventional face masks have a cone-shape mount with a soft cuff extending around its edge, which is applied against the skin of the patient around the nose and mouth. A port opens into the interior of the mount so that air or other gas can be supplied to the patient's nose and mouth. Usually, these face masks are held against the face manually or by means of a strap extending around the patient's head. The pressure needed to ensure an effective seal can cause damage to the patient's skin. It can also be difficult to achieve an effective seal without applying manual pressure; this is a disadvantage because it occupies a nurse or clinician. Alternatively, it has been proposed in U.S. Pat. No. 3,357,426 and WO99/25410 that a face mask be secured to the patient's face by means of an adhesive.

BRIEF SUMMARY OF THE INVENTION

It is an object of the present invention to provide an alternative ventilation device.

According to the present invention there is provided a patient ventilation device including a member adapted to extend across the mouth and nose of a patient, the device having an opening through the member in the region of the mouth, and the member having an adhesive surface adapted to seal around the mouth and nose of the patient such that the nose is blocked and the mouth opens through the opening enabling ventilation via the mouth.

The member preferably includes a flexible sheet, which may have two laterally-extending cheek pads and a nose pad with a plurality of split lines enabling it to be shaped around the nose. The opening may be provided by a tube, one end of the tube extending within the patient's mouth and the other end projecting externally. The adhesive may include a hydrocolloid. Alternatively, the member may include a sac of flexible material having a closed end and an open end adapted to be applied to the face of the patient around the nose and mouth, the sac containing a filling of a conformable material adapted to mould to the contours of the face. The conformable material may be a gel. The adhesive may be in an outer layer of the sac and the conformable material may be within the adhesive.

Ventilation devices according to the present invention, will now be described, by way of example, with reference to the accompanying drawings.

BRIEF DESCRIPTION OF THE DRAWINGS

FIG. 1 is a perspective view of the rear of a first device before use;

FIG. 2 is a side elevation view of the device of FIG. 1 in use;

DETAILED DESCRIPTION OF PREFERRED EMBODIMENTS

Figure 3:
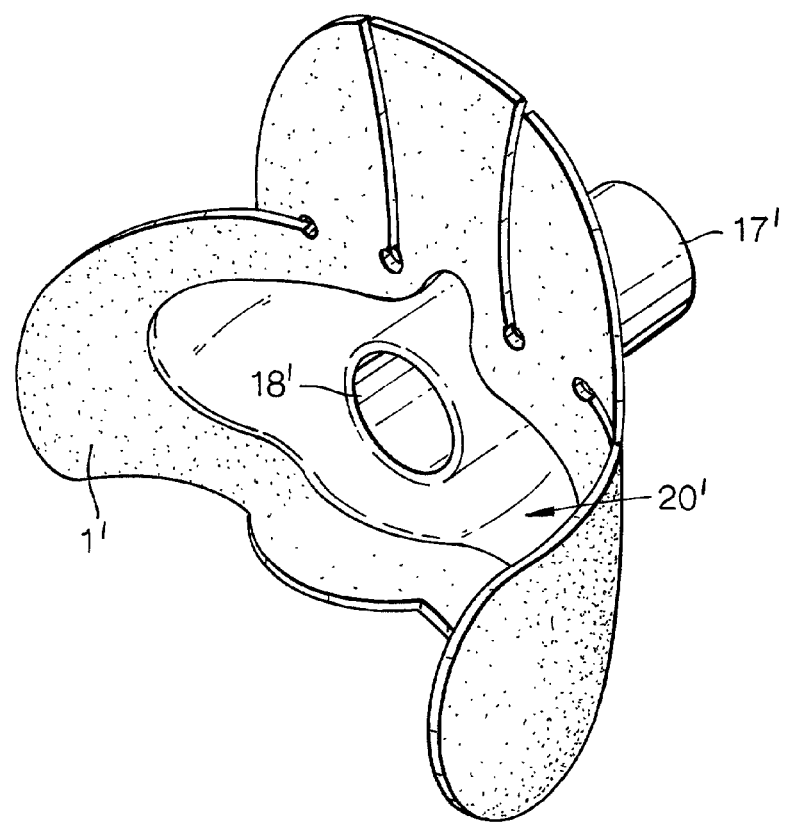
FIG. 3 is a perspective view of the rear of a modification of the device shown in FIGS. 1 and 2.

With reference first to FIGS. 1 and 2, the device takes the form an adhesive face mask arranged to block the nose and enable ventilation through the mouth. The device comprises a flexible sheet or plate 1 the rear surface 10 of which is adhesive, such as in the form of a hydrocolloid or other skin-compatible adhesive. The plate 1 has two cheek pads 11 and 12 extending laterally on opposite sides, a small, semi-circular, downwardly-projecting chin pad 13 and a larger upwardly-projecting nose pad 14. The nose pad 14 has four split lines 15 to enable it to be shaped about the nose. The device also has an opening through the plate 1 in the form of a short, rigid, tubular plastics fitting 16 secured to the plate and projecting through it at a location centrally across its width, so that it is in line with the mouth. The fitting 16 enables a vent tube 17 to be inserted, the vent tube having one end 18 that extends into and opens within the mouth and an opposite end 19 that projects externally forwardly from the device. In use, the forward end 19 of the tube is either left open, when the patient is breathing spontaneously, or is connected to ventilation or anaesthesia equipment, when necessary. The vent tube 17 can be removed from the fitting 16 when not required, such as when initially securing the device to the patient's face. Alternatively, the device could have a vent tube permanently fixed with the plate 1. The device is fitted by aligning the fitting 16 with the patient's mouth and smoothing the pads 11 to 14 onto the skin. The vent tube 17 can then be inserted.

With reference now to FIG. 3, there is shown a modified form of the device in which the plate 1' has a central region 20' that is non-adhesive, clear and transparent so that the region around the mouth can be viewed by the clinician. This region 20' may be a flexible film or a rigid clear plastics. The outer part of the plate 1' is flexible and adhesive. FIG. 3 shows a vent tube 17' permanently fixed with the plate 1' and having a patient end 18' terminating flush with the patient-side surface of the plate, so that it does not extend within the mouth.

Figure 4:
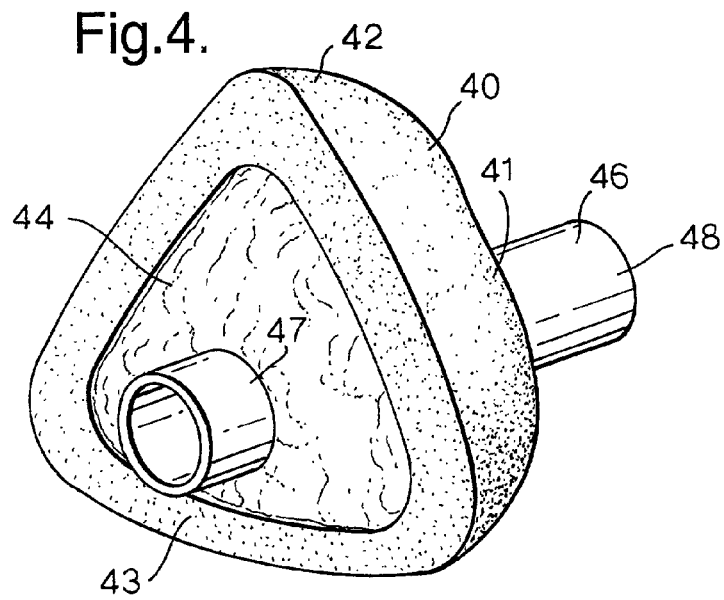
FIG. 4 is a perspective view of the rear of an alternative device.

With reference now to FIG. 4 there is shown an alternative form of ventilation device. This comprises an outer sac 40 of a flexible material such as rubber or silicone rubber, which has a substantially triangular section and tapers in width from its closed forward end 41 to its open rear or patient end 42. The size and shape of the rear end 42 of the sac 40 are such that it can fit around the nose and mouth of the patient. The sac 40 is filled with two different materials. It contains an outer layer 43 of an adhesive, such as a hydrocolloid, and an inner mass 44 of a conformable material, such as a gel. The hydrocolloid layer 43 is relatively thick, typically around 10 mm, so that the rear face of the device presents an adhesive annular, peripheral region that is sufficiently wide to ensure secure retention on the skin. The adhesive layer need not extend around the entire inner surface of the sac 40 providing that it forms an adhesive peripheral region around the open end 42 of the sac. Instead of the adhesive being inside the sac, it could, for example, be provided on an externally-projecting flange. The device is completed by a vent tube 46 extending along the sac 40 through the gel 44. The rear end 47 of the tube 46 projects a short distance from the open end 42 of the sac 40 so that it extends into the patient's mouth. The forward end 48 of the tube 46 projects externally from the forward end of the device to enable connection to ventilation equipment.

The gel 44 and adhesive 43 are protected by a release sheet (not shown), which is removed just before use. The device is then held up to the patient's face and the rear end 47 of the vent tube 46 is located in the patient's mouth. The device is pressed firmly against the face so that the gel 44 moulds about the contours of the nose and mouth and so that the adhesive 43 bonds with the skin. Once firmly in position, the device can be released since it is self-supporting.

The arrangements of the present invention enable reliable ventilation via the mouth without the need for continuous manual pressure and without the need for straps or the like, which can cause skin damage after prolonged use. The device of the invention can be used on patients of differing builds without the need to provide a wide range of different sizes.

What we claim is:

1. A patient ventilation device comprising: a flexible, adhesive sheet member adapted to extend across the mouth and nose of a patient; an opening through said member in the region of the mouth; and an adhesive surface on the member adapted to seal around the mouth and including adhesive adapted to directly adhere to the nose to close the nose of the patient such that the nose is blocked by adhesion of said flexible, adhesive sheet member around the nose and the mouth opens through said opening enabling ventilation via the mouth.

2. A device according to claim 1, wherein said sheet has two laterally-extending cheek pads.

3. A device according to claim 1, wherein said sheet has a nose pad with a plurality of split lines enabling it to be shaped around the nose.

4. A device according to claim 1, wherein the device includes a tube, wherein said opening is provided by said tube, and wherein one end of said tube extends within the patient's mouth and another end of said tube projects externally.

5. A device according to claim 1, wherein said adhesive includes a hydrocolloid.

6. A patient ventilation device comprising: a flexible adhesive sheet shaped to extend across the mouth and nose of a patient; a tubular fitting attached with said flexible, adhesive sheet, said tubular fitting having an opening extending through said sheet in the region of the mouth, said adhesive sheet including adhesive adapted to directly adhere to the nose such that the nose is blocked by said sheet extending over the nose and contacting adhesively around the nose and the mouth opens through said opening enabling ventilation via the mouth.

7. A device according to claim 6 including a removable vent tube inserted through said fitting.

* * * * *